(12) United States Patent
Lin et al.

(10) Patent No.: US 11,023,718 B2
(45) Date of Patent: Jun. 1, 2021

(54) LIVING BODY DETECTION METHOD AND LIVING BODY DETECTION SYSTEM

(71) Applicant: Wistron Corporation, New Taipei (TW)

(72) Inventors: Zhao-Yuan Lin, New Taipei (TW); Yao-Tsung Chang, New Taipei (TW); Zhe-Yu Lin, New Taipei (TW)

(73) Assignee: Wistron Corporation, New Taipei (TW)

( * ) Notice: Subject to any disclaimer, the term of this patent is extended or adjusted under 35 U.S.C. 154(b) by 129 days.

(21) Appl. No.: 16/429,079

(22) Filed: Jun. 3, 2019

(65) Prior Publication Data

US 2020/0320286 A1    Oct. 8, 2020

(30) Foreign Application Priority Data

Apr. 2, 2019    (TW) .................................. 108111598

(51) Int. Cl.
*G06K 9/00*    (2006.01)
*A61B 5/1171*    (2016.01)
*G01S 13/89*    (2006.01)

(52) U.S. Cl.
CPC ........ *G06K 9/00369* (2013.01); *A61B 5/1171* (2016.02); *G01S 13/89* (2013.01)

(58) Field of Classification Search
CPC .... A61B 5/1171; G01S 13/89; G06K 9/00369
See application file for complete search history.

(56) References Cited

U.S. PATENT DOCUMENTS

| | | | | |
|---|---|---|---|---|
| 2018/0183650 A1* | 6/2018 | Zhang | ................... | G01S 13/003 |
| 2019/0158340 A1* | 5/2019 | Zhang | ................... | H04B 17/318 |
| 2019/0175074 A1* | 6/2019 | Zhang | ................... | H04B 17/336 |
| 2019/0327124 A1* | 10/2019 | Lai | ........................ | H04L 27/362 |

FOREIGN PATENT DOCUMENTS

| | | |
|---|---|---|
| CN | 1713274 | 12/2005 |
| CN | 103606248 | 2/2014 |

OTHER PUBLICATIONS

"Office Action of Taiwan Counterpart Application", dated Jul. 20, 2020, p. 1-p. 9.

* cited by examiner

*Primary Examiner* — Tom Y Lu
(74) *Attorney, Agent, or Firm* — JCIPRNET

(57) ABSTRACT

A living body detection method and a living body detection system are provided. A radio-frequency signal reflected by an experiment living body is received, and raw sampling data of the RF signal are obtained. A feature extraction process is performed to generate initial training features of sampling datasets, wherein the initial training features respectively correspond to feature generation rules. A classification prediction model is established according to a posture of the experiment living body and the initial training features, and correlation feature weightings respectively corresponding to the initial training features are obtained. Preferred features corresponding to at least one of the feature generation rules are selected from the initial training features according to the correlation feature weightings. Another classification prediction model configured for determining a posture of a detection living body is established according to the posture of the experiment living body and the preferred features.

22 Claims, 4 Drawing Sheets

LIVING BODY DETECTION METHOD AND LIVING BODY DETECTION SYSTEM

CROSS-REFERENCE TO RELATED APPLICATION

This application claims the priority benefit of Taiwan application serial no. 108111598, filed on Apr. 2, 2019. The entirety of the above-mentioned patent application is hereby incorporated by reference herein and made a part of this specification.

BACKGROUND

Technical Field

The disclosure relates to a living body detection method and a living body detection system, and more particularly, to a living body detection method and a living body detection system based on machine learning.

Description of Related Art

In recent years, non-contact sensing modules have been applied to measure physiological information of the human body to assist in monitoring the heartbeat and breathing conditions of the human body, and have the advantages of instant, non-contact, extended, and continuous monitoring. Specifically, the human body generates slight physiological movements all the time, such as the periodical movement of the chest caused by the heartbeat and the breathing with lungs. If the human body is irradiated with electromagnetic waves by a radar, according to the Doppler effect, these contraction and extension movements of the human muscle will cause phase changes in the electromagnetic waves upon reflection. Therefore, according to the difference information between the emitted RF signal of the radar and the reflected RF signal generated by the reflection on the human body, the non-contact sensing module can detect physiological information of the human body.

SUMMARY

The difference information between the emitted RF signal and the reflected RF signal can be used not only to detect physiological information of the human body such as the heartbeat, pulse, and breathing, but also to detect the physical movement or posture of the human body. However, in order to detect the changeable physical movement or posture according to the reflected RF signal generated by the reflection on the human body, in addition to hardware considerations, how to establish an accurate and efficient analysis algorithm to determine the physical movement or posture of the human body is also an issue of concern to those skilled in the art.

In view of the above, the disclosure provides a living body detection method and a living body detection system that can reduce the computational complexity in the detection of a posture of a living body according to an RF signal and machine learning.

An embodiment of the disclosure provides a living body detection method including steps below. An RF signal reflected by an experiment living body is received, and a plurality of raw sampling data of the RF signal are generated. A feature extraction process is performed according to the raw sampling data to generate a plurality of initial training features of a plurality of sampling datasets, wherein the initial training features respectively correspond to a plurality of feature generation rules. A classification prediction model is established according to a posture of the experiment living body and the initial training features, and a plurality of correlation feature weightings respectively corresponding to the initial training features are obtained. A plurality of preferred features corresponding to at least one of the feature generation rules are selected from the initial training features according to the correlation feature weightings. Another classification prediction model is established according to the posture of the experiment living body and the preferred features. A posture of a detection living body is determined based on the another classification prediction model.

From another perspective, an embodiment of the disclosure provides a living body detection system including an antenna, an RF signal processing circuit, a storage circuit, and a processor. The antenna receives an RF signal reflected by an experiment living body. The RF signal processing circuit is coupled to the antenna and generates a plurality of raw sampling data of the RF signal. The storage circuit stores a plurality of modules. The processor is coupled to the storage circuit and the RF signal processing circuit and accesses the modules in the storage circuit to perform steps below. A feature extraction process is performed according to the raw sampling data to generate a plurality of initial training features of a plurality of sampling datasets, wherein the initial training features respectively correspond to a plurality of feature generation rules. A classification prediction model is established according to a posture of the experiment living body and the initial training features, and a plurality of correlation feature weightings respectively corresponding to the initial training features are obtained. A plurality of preferred features corresponding to at least one of the feature generation rules are selected from the initial training features according to the correlation feature weightings. Another classification prediction model is established according to the posture of the experiment living body and the preferred features. A posture of a detection living body is determined based on the another classification prediction model.

Based on the above, in the embodiments of the disclosure, the posture of the human body can be accurately determined according to the classification prediction model trained by machine learning. In addition, in the embodiments of the disclosure, as ensuring that the classification accuracy of the classification prediction model is maintained at a certain level, a part of the available features may be flexibly selected to reduce the data computation amount, which contributes to reduction of the computation amount required for machine learning and realization of rapid detection.

To make the aforementioned more comprehensible, several embodiments accompanied with drawings are described in detail as follows.

DESCRIPTION OF THE EMBODIMENTS

Figure 1:
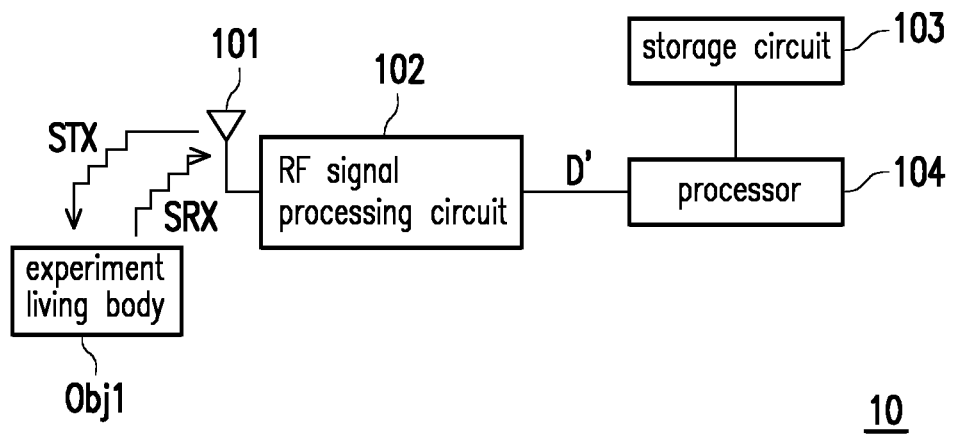
FIG. 1 is a schematic view of a living body detection system according to an embodiment of the disclosure.

Some embodiments of the disclosure will next be detailed with reference to the accompanying drawings. The same reference numerals used in different drawings will be regarded as referring to the same or similar components. The embodiments only form part of the disclosure and do not disclose all of the embodiments that can be implemented according to the disclosure. More specifically, the embodiments are only examples of the living body detection method and the living body detection system according to the claims herein.

FIG. 1 is a schematic view of a living body detection system 10 according to an embodiment of the disclosure. Referring to FIG. 1, the living body detection system 10 includes an antenna 101, a radio-frequency (RF) signal processing circuit 102, a storage circuit 103, and a processor 104. In the present embodiment, the living body detection system 10 may detect a posture of a human body or a posture of another living body with vital signs according to radar sensing techniques. The living body detection system 10 may include a continuous waveform (CW) radar to emit an emitted RF signal which is a continuous wave toward the living body and receive a reflected RF signal generated from the emitted RF signal reflected by the living body. In another embodiment, the radar of the living body detection system 10 may be an ultra-wideband (UWB) radar or a frequency modulated continuous waveform (FMCW) radar, and the corresponding antenna framework is replaced.

Specifically, the antenna 101 is configured to emit and/or receive a wireless RF signal. It is noted that the disclosure does not limit the number of the antenna. In the embodiments of the disclosure, the antenna 101 may receive an RF signal SRX reflected by an experiment living body Obj1. The experiment living body Obj1 may be a human body or another creature with vital signs, and the disclosure is not limited thereto. More specifically, the antenna 101 or another antenna emits an RF signal STX toward the experiment living body Obj1, and the antenna 101 receives the RF signal SRX generated from the RF signal STX reflected by the experiment living body Obj1. Since the RF signal STX is affected by breathing, heartbeat fluctuations, or limb movements of the experiment living body Obj1, the phase of the reflected RF signal SRX will be different from the phase of the RF signal STX.

Figure 2:
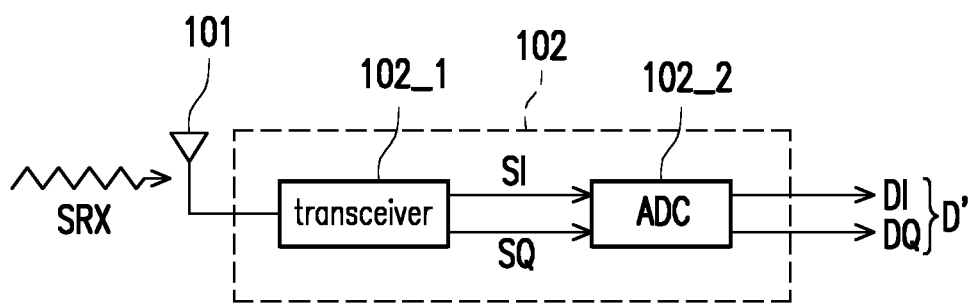
FIG. 2 is a schematic view of an RF signal processing circuit according to an embodiment of the disclosure.

The RF signal processing circuit 102 is coupled to the antenna 101, processes the RF signal SRX received by the antenna 101, and generates a plurality of raw sampling data D' of the RF signal SRX. Specifically, FIG. 2 is a schematic view of the RF signal processing circuit according to an embodiment of the disclosure. Referring to FIG. 2, the RF signal processing circuit 102 may include a transceiver 102_1 and an analog-digital converter (ADC) 102_2. The transceiver 102_1 is coupled to the antenna 101 and may generate a baseband output signal according to the RF signal SRX. Next, the baseband output signal generated by the transceiver 102_1 is converted into digital data. In the present embodiment, the transceiver 102_1 may include a quadrature demodulator having a frequency mixer and an oscillator, and the RF signal SRX is down-converted into an in-phase polarized signal SI of the in-phase-channel (I-channel) and a quadrature polarized signal SQ of the quadrature-channel (Q-channel) through a mixing process in the quadrature demodulator. Then, the analog-digital converter 102_2 may respectively sample the in-phase polarized signal SI and the quadrature polarized signal SQ to generate in-phase polarized discrete data DI and quadrature polarized discrete data DQ. In other words, the raw sampling data D' generated by the RF signal processing circuit 102 may include the in-phase polarized discrete data DI and the quadrature polarized discrete data DQ.

The storage circuit 103 is, for example, a fixed or movable random access memory (RAM), read-only memory (ROM), flash memory, hard disk in any form, another similar device, or a combination of these devices, and may be configured to record multiple program code or modules.

The processor 104 is coupled to the storage circuit 103 and the RF signal processing circuit 102 and receives the raw sampling data D' provided by the RF signal processing circuit 102. In the embodiments of the disclosure, at the stage of training a classification prediction model, the processor 104 may first train the classification prediction model according to the raw sampling data D' associated with the experiment living body Obj1 and the known posture of the experiment living body Obj1. Then, at the implement stage of actual detection, the processor 104 may then perform the posture detection according to the trained classification prediction model and the RF signal reflected by a detection living body. The processor 104 may be a general-purpose processor, a specific-purpose processor, a conventional processor, a digital signal processor, a plurality of microprocessors, one or more microprocessors combined with digital signal processor cores, a controller, a microcontroller, an application specific integrated circuit (ASIC), a field programmable gate array (FPGA), an integrated circuit of any other type, a state machine, a processor based on Advanced RISC Machine (ARM), or a similar device. In the embodiments of the disclosure, the processor 104 may load the program codes or modules recorded in the storage circuit 103 to perform the living body detection method provided herein, which will be further described with reference to flowcharts.

In another embodiment of the disclosure, the living body detection system 10 may further include a communication interface which may transmit the raw sampling data D' generated by the RF signal processing circuit 102 to an analyzer via a network (e.g., the Internet).

The communication interface may be a wired communication interface such as a universal asynchronous receiver-transmitter (UART), an inter-integrated circuit bus (I2C), a serial peripheral interface (SPI), a controller area network (CAN), the Recommended Standard (RS) 232, the Recommended Standard (RS) 422, etc. The communication interface may also be a wireless communication interface such as a wireless sensing network (e.g., EnOcean/Bluetooth/ZigBee), a honeycomb network (e.g., 2G/3G/Long-Term Evolution (LTE)/5G), a wireless local area network (e.g., wireless local area network (WLAN)/Worldwide Interoperability for Microwave Access (WiMAX)), short-range point-to-point communication (e.g., radio frequency identification (RFID)/EnOcean/near field communication (NFC)), etc., but the disclosure is not limited thereto. The analyzer may be a cloud server, a data computing center, etc., but the disclosure is not limited thereto. Accordingly, the analyzer can collect the raw sampling data D' corresponding to different experiment living bodies Obj1 detected by different living body detection systems 10 and perform the living body detection method herein to process the plurality of raw sampling data D'.

Figure 3:
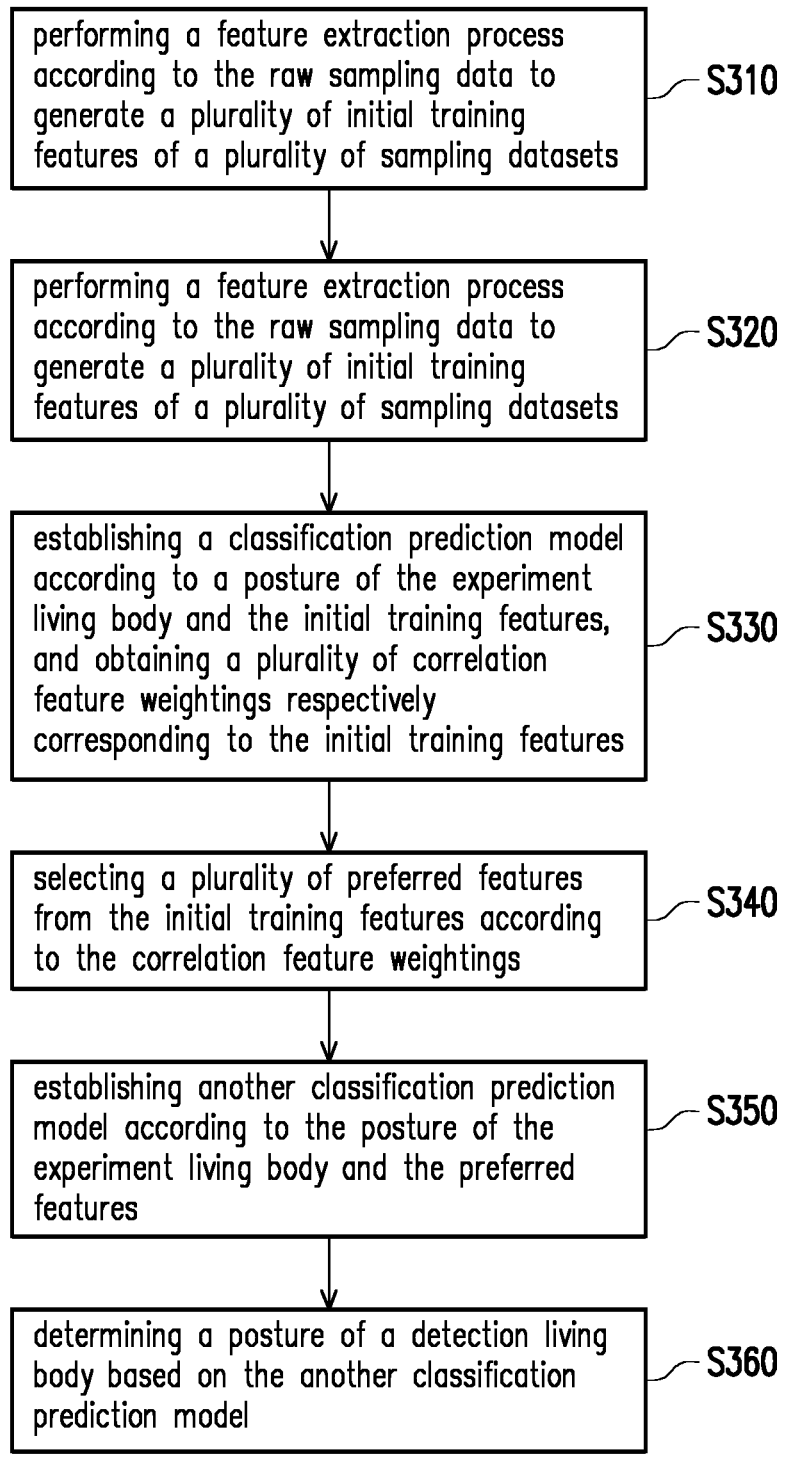
FIG. 3 is a flowchart of a living body detection method according to an embodiment of the disclosure.

FIG. 3 is a flowchart of a living body detection method according to an embodiment of the disclosure. Referring to FIG. 1 and FIG. 3, the method of the present embodiment is applicable to the living body detection system 10 of the above embodiment, and the detailed steps of the living body detection method of the present embodiment will be described below with reference to the components in the living body detection system 10.

In step S310, the antenna 101 receives an RF signal SRX reflected by an experiment living body Obj1, and the RF signal processing circuit 102 generates a plurality of raw sampling data D' of the RF signal SRX. The RF signal processing circuit 102 down-converts the RF signal SRX into a baseband signal and then performs sampling to generate the plurality of raw sampling data D'. If the RF signal processing circuit 102 demodulates the RF signal SRX into an in-phase polarized signal and a quadrature polarized signal, then the raw sampling data D' may include in-phase polarized discrete data corresponding to the I-channel and quadrature polarized discrete data corresponding to the Q-channel.

In step S320, the processor 104 performs a feature extraction process according to the raw sampling data to generate a plurality of initial training features of a plurality of sampling datasets. It is noted that the processor 104 may sample a series of raw sampling data D' into a plurality of sampling datasets, and the sampling datasets may respectively include the raw sampling data D' of the same number. For example, the sampling datasets may respectively include 250 entries of raw sampling data D', but the disclosure is not limited thereto. In addition, the raw sampling data in two sampling datasets having adjacent sampling time will partially overlap with each other. The processor 104 performs the feature extraction process according to the raw sampling data in each of the sampling datasets to generate the plurality of initial training features for each of the sampling datasets. The initial training features respectively correspond to a plurality of feature generation rules. In other words, the processor 104 may generate the initial training features for each of the sampling datasets according to a plurality of predetermined feature generation rules.

In step S330, the processor 104 establishes a classification prediction model according to a posture of the experiment living body Obj1 and the initial training features, and obtains a plurality of correlation feature weightings respectively corresponding to the initial training features. In the present embodiment, the processor 104 may establish the classification prediction model by using the posture of the experiment living body Obj1 and the initial training features as training data for a supervised learning algorithm. The supervised learning algorithm is, for example, a support vector machine (SVM) algorithm. Specifically, at the stage of training the classification prediction model, the processor 104 may label the sampling datasets based on the posture of the experiment living entity Obj1 and use the initial training features of the labeled sampling datasets as the training material for machine learning.

Here, the correlation feature weightings respectively corresponding to the initial training features are generated based on the kernel function that is operated with the supervised learning algorithm. The kernel function is, for example, the radial basis function kernel for performing dimensionality reduction mapping, but the disclosure is not limited thereto. In detail, when the processor 104 trains the classification prediction model by using the kernel function and the supervised learning algorithm, the correlation feature weighting of each of the initial training features is also generated. The importance of each of the initial training features is directly reflected by the correlation feature weighting. Specifically, the larger the absolute value of the correlation feature weighting is, the more representative the initial training feature is.

In step S340, the processor 104 selects, from the initial training features, a plurality of preferred features corresponding to at least one of the feature generation rules according to the correlation feature weightings. It is known that the larger the absolute value of the correlation feature weighting is, the more important the corresponding initial training feature is for the correct classification. Therefore, the processor 104 may select a part of the initial training features as the preferred features according to the correlation feature weightings to further omit the less necessary features. Next, in step S350, the processor 104 establishes another classification prediction model according to the posture of the experiment living body Obj1 and the selected preferred features. In other words, through the supervised learning algorithm, the processor 104 can train another classification prediction model according to the selected preferred features and the posture of the experiment living body Obj1.

On this basis, in step S360, the processor 104 determines a posture of a detection living body based on the another classification prediction model. Specifically, the processor 104 may apply the another classification prediction model to the actual detection, and determine the posture of the detection living body according to the RF signal reflected by the detection living body based on the another classification prediction model. It is known that since the preferred features for training the another classification prediction model are generated through filtering, the processor 104 only needs to generate features for detecting the posture of the living body according to the feature generation rules of the preferred features, which thereby reduces the data computation costs.

It is noted that, as an example, the embodiment shown in FIG. 3 performs a one-time filtering on the initial training features. However, in other embodiments, the processor 140 may repetitively perform the training of the classification prediction model and the filtering of the preferred features to generate a classification prediction model that is ultimately applied to the actual detection. For example, after performing step S350 and training the another classification prediction model, the processor 104 may obtain the correlation feature weightings respectively corresponding to the preferred features. Then, the processor 104 may perform feature selection again according to the correlation feature weightings respectively corresponding to the preferred features, and establish still another classification prediction model to apply the still another classification prediction model to the actual detection.

Figure 4A:
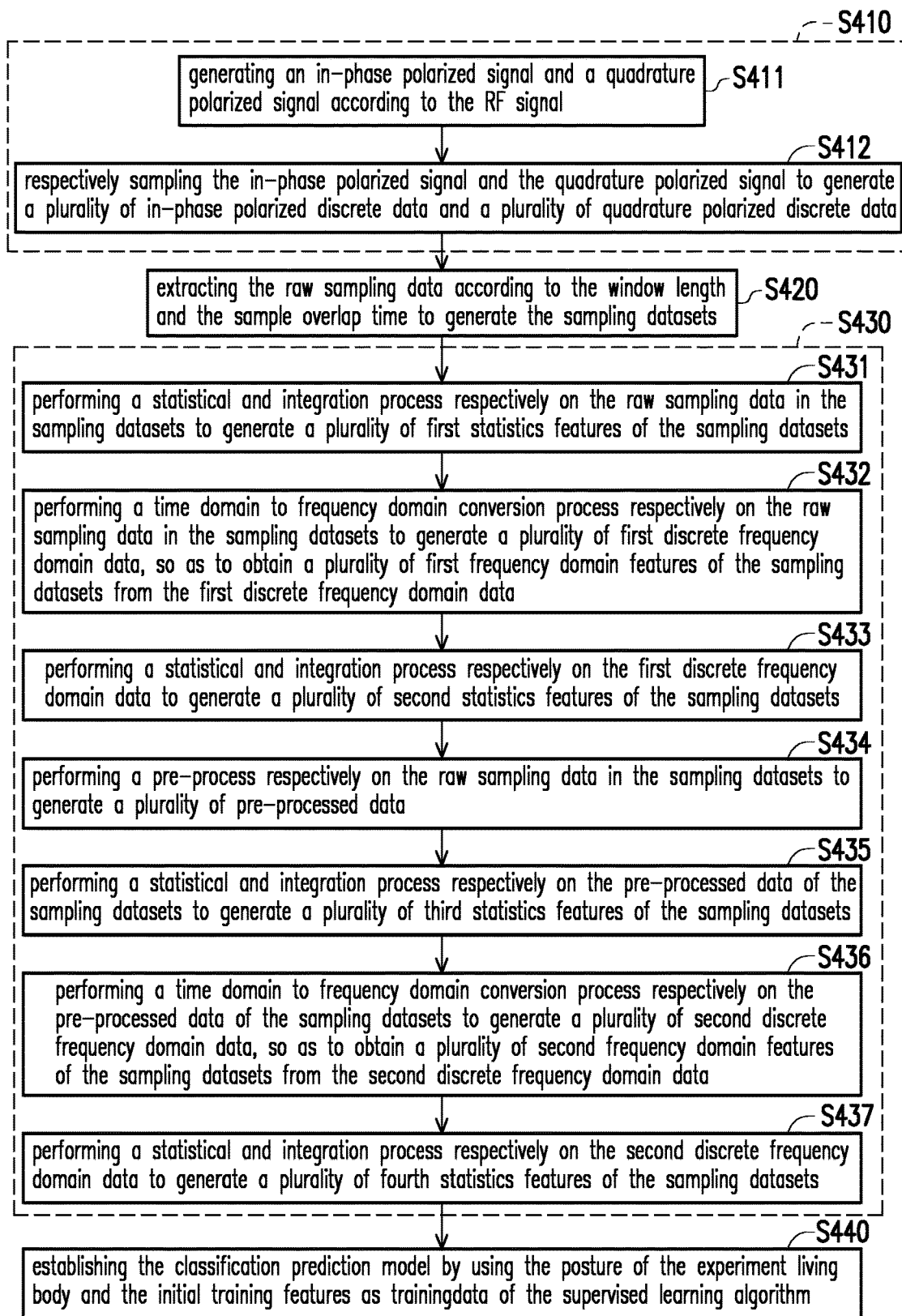
FIG. 4A and FIG. 4B are flowcharts of a living body detection method according to an embodiment of the disclosure.
Figure 4B:
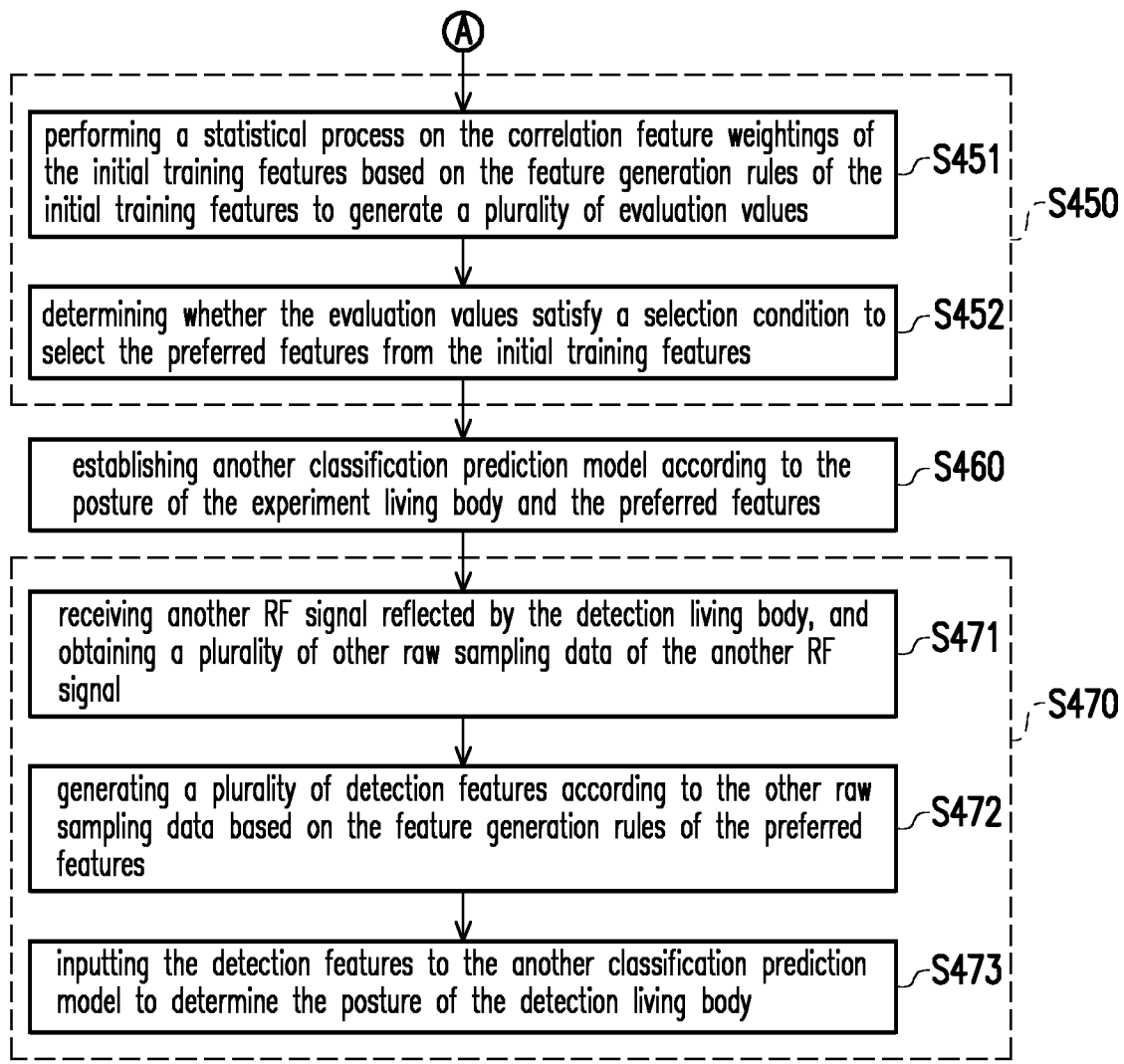

Details of the above process and implementation will be described below with reference to FIG. 4A and FIG. 4B. FIG. 4A and FIG. 4B are flowcharts of a living body detection method according to an embodiment of the disclosure. The application scenario of the present embodiment may be safety monitoring of an infant or care of a patient. The living body detection system 10 may be used to detect whether the sleep posture of an infant or a patient is lying face-up or lying face-down, but the disclosure is not limited thereto. The antenna 101 of the living body detection system 10 is adapted to be installed above a bed or close to a bed in a home environment, at a hospital, at a care center, etc. for safety monitoring purposes.

Referring to FIG. 1, FIG. 2, and FIG. 4A at the same time, in step S410, the RF signal processing circuit 102 receives an RF signal SRX reflected by an experiment living body Obj1 and generates a plurality of raw sampling data D' of the RF signal SRX. The experiment living body Obj1 may be a human body lying on a bed. Specifically, in the present embodiment, in step S411, the transceiver 102_1 of the RF signal processing circuit 102 generates an in-phase polarized signal SI and a quadrature polarized signal SQ according to the RF signal SRX. In step S412, the analog-digital converter 102_2 respectively samples the in-phase polarized signal SI and the quadrature polarized signal SQ to generate a plurality of in-phase polarized discrete data DI and a plurality of quadrature polarized discrete data DQ.

The processor 104 receives the plurality of in-phase polarized discrete data DI and the plurality of quadrature polarized discrete data DQ from the RF signal processing circuit 102. In step S420, the processor 104 extracts the raw sampling data according to the window length, the sample size, and the sample overlap time to generate the sampling datasets. In other words, the processor 104 samples the in-phase polarized discrete data DI and the quadrature polarized discrete data DQ according to the window length, the sample size, and the sample overlap time to generate the sampling datasets including the in-phase polarized discrete data DI and the quadrature polarized discrete data DQ.

The sampling datasets include a first sampling dataset and a second sampling dataset which have adjacent extraction time. In other words, based on the sampling sequence, the second sampling dataset may be the next set of sampling content of the first sampling dataset. The raw sampling data in the first sampling dataset partially overlaps with the raw sampling data in the second sampling dataset. The extraction time of the first sampling dataset differs from the extraction time of the second sampling dataset by a predetermined time interval, and the predetermined time interval is determined according to the sample size and the sample overlap time. Table 1 is a sampling example of the sampling datasets according to an embodiment of the disclosure. It is assumed here that 50 entries of raw sampling data may be sampled per second, but the disclosure is not limited thereto.

TABLE 1

| Window length | Sample size | Sample overlap time |
| --- | --- | --- |
| 1500 entries (30 seconds) | 800 entries (16 seconds) | 600 entries (12 seconds) |
| 250 entries (5 seconds) | 150 entries (3 seconds) | 100 entries (2 seconds) |

As shown in Table 1, Table 1 illustrates extraction examples of two types of sampling datasets. Each of the sampling datasets includes raw sampling data in a data amount that matches the sample size. The window length for sampling the first type of sampling dataset is 30 seconds, and the first type of sampling dataset has 800 entries of raw sampling data. In addition, in the case where each sampling dataset has 600 entries of identical repetitive data with respect to the next sampling dataset (i.e., 12 seconds of overlapping sampling time), the extraction time of each sampling dataset differs from the extraction time of the next sampling dataset by 4 seconds. On the other hand, the window length for sampling the second type of sampling dataset is 5 seconds, and the second type of sampling dataset has 150 entries of raw sampling data. In the case where each sampling dataset has 100 entries of identical repetitive data with respect to the next sampling dataset (i.e., 2 seconds of overlapping sampling time), the extraction time of each sampling dataset differs from the extraction time of the next sampling dataset by 1 second.

In step S430, the processor 104 performs a feature extraction process according to the raw sampling data to generate a plurality of initial training features of the plurality of sampling datasets. In the present embodiment, the processor 104 may obtain the initial training features corresponding to different feature generation rules through the statistical and integration process, the time domain to frequency domain conversion process, and the pre-process in the feature extraction process. In the present embodiment, the initial training features corresponding to the different feature generation rules may include a first statistics feature, a second statistics feature, a third statistics feature, a fourth statistics feature, a first frequency domain feature, and a second frequency domain feature. In addition, it is noted that the processor 104 also performs the feature extraction process on the sampling dataset including the in-phase polarized discrete data DI and the sampling dataset including the quadrature polarized discrete data DQ to generate the initial training feature associated with the I-channel data and the initial training feature associated with the Q-channel data.

Specifically, in step S431, the processor 104 performs a statistical and integration process respectively on the raw sampling data in the sampling datasets to generate a plurality of first statistics features of the sampling datasets. The statistical and integration process may include one of a mean value operation, taking a maximum value, taking a minimum value, a standard deviation operation, a kurtosis operation, a skew value operation, taking a quartile, a mean absolute deviation (MAD) operation, calculation of an area according to the Trapz function, calculation of a square of the area according to the Trapz function, or a combination thereof. For example, the processor 104 may perform the mean value process and take the maximum value respectively on the raw sampling data in each of the sampling datasets to use the mean value and the maximum value of the raw sampling data in each of the sampling datasets as the first statistics features. Alternatively, the processor 104 may perform the standard deviation operation, the skew value operation, and the calculation of the area according to the Trapz function respectively on the raw sampling data in each of the sampling datasets to use the standard deviation, the skew value, and the output area of the Trapz function of the raw sampling data in each of the sampling datasets as the first statistics features. In other words, the first statistics features are generated based on the statistical and integration process.

In step S432, the processor 104 performs a time domain to frequency domain conversion process respectively on the raw sampling data in the sampling datasets to generate a plurality of first discrete frequency domain data, so as to obtain a plurality of first frequency domain features of the sampling datasets from the first discrete frequency domain data. The time domain to frequency domain conversion process may be the discrete Fourier transform (DFT). After the discrete Fourier transform is performed on the raw sampling data in the sampling datasets, the processor 104 can obtain the plurality of first discrete frequency domain data for indicating a plurality of frequency components. The first discrete frequency domain data includes discrete Fourier coefficients. The processor 104 may take the discrete Fourier coefficients and the corresponding frequencies of a part of the first discrete frequency domain data as the first frequency domain features. The processor 104 may also generate weighted mean frequencies according to the first discrete frequency domain data as the first frequency domain features. In other words, the first frequency domain features are generated based on the time domain to frequency domain conversion process.

In step S433, the processor 104 performs a statistical and integration process respectively on the first discrete frequency domain data to generate a plurality of second statistics features of the sampling datasets. In other words, the processor 104 may further process the first discrete frequency domain data generated through the discrete Fourier transform to generate the second statistics features. The statistical and integration process performed in step S433 may be the same or different from the statistical and integration process performed in step S431. For example, the processor 104 may perform the mean value operation on the first discrete frequency domain data of the raw sampling data in each of the sampling datasets to use the mean values of the first discrete frequency domain data as the second statistics features. The processor 104 first performs the time domain to frequency domain conversion process and then performs the statistical and integration process to generate the plurality of second statistics features of the sampling datasets. In other words, the second statistics features are generated based on the time domain to frequency domain conversion process and the statistical and integration process.

In step S434, the processor 104 performs a pre-process respectively on the raw sampling data in the sampling datasets to generate a plurality of pre-processed data. The pre-process is, for example, a jerk operation, and the processor 104 may perform a jerk operation respectively on the raw sampling data in the sampling datasets to convert the raw sampling data of each of the sampling datasets into a plurality of jerk data.

In step S435, the processor 104 performs a statistical and integration process respectively on the pre-processed data of the sampling datasets to generate a plurality of third statistics features of the sampling datasets. The statistical and integration process performed in step S435 may be the same or different from the statistical and integration process performed in step S431. The processor 104 first performs the pre-process and then performs the statistical and integration process to generate the plurality of third statistics features of the sampling datasets. In other words, the third statistics features are generated based on the pre-process and the statistical and integration process.

In step S436, the processor 104 performs a time domain to frequency domain conversion process respectively on the pre-processed data of the sampling datasets to generate a plurality of second discrete frequency domain data, so as to obtain a plurality of second frequency domain features of the sampling datasets from the second discrete frequency domain data. The processor 104 first performs the pre-process and then performs the time domain to frequency domain conversion process to generate the plurality of second frequency domain features of the sampling datasets. In other words, the second frequency domain features are generated based on the pre-process and the time domain to frequency domain conversion process.

In step S437, the processor 104 performs a statistical and integration process respectively on the second discrete frequency domain data to generate a plurality of fourth statistics features of the sampling datasets. In other words, the processor 104 first performs the pre-process and the time domain to frequency domain conversion process and then performs the statistical and integration process to generate the plurality of fourth statistics features of the sampling datasets. In other words, the fourth statistics features are generated based on the pre-process, the time domain to frequency domain conversion process, and the statistical and integration process.

It is assumed that the statistical and integration process may include 10 operations, i.e., the mean value operation, taking the maximum value, taking the minimum value, the standard deviation operation, the kurtosis operation, the skew value operation, taking the quartile, the mean absolute deviation operation, the calculation of the area according to the Trapz function, and the calculation of the square of the area according to the Trapz function. Also, it is assumed that the processor 104 takes the weighted mean frequency, the first five discrete Fourier coefficients, and the first five local maximum values among the discrete Fourier coefficients and the corresponding frequencies as the frequency domain features. In addition, it is assumed that the pre-process is the jerk operation. Table 2 is an example of the initial training features generated based on the above assumptions.

TABLE 2

| Feature No. | Description |
|---|---|
| 0-9 | 10 initial training features (i.e., the first statistics features) generated by performing the statistical and integration process on the in-phase polarized discrete data in one sampling dataset |
| 10-19 | 10 initial training features (i.e., the first statistics features) generated by performing the statistical and integration process on the quadrature polarized discrete data in one sampling dataset |
| 20-29 | 10 initial training features (i.e., the third statistics features) generated by performing the jerk operation and the statistical and integration process on the in-phase polarized discrete data in one sampling dataset |
| 30-39 | 10 initial training features (i.e., the third statistics features) generated by performing the jerk operation and the statistical and integration process on the quadrature polarized discrete data in one sampling dataset |
| 40-49 | 10 initial training features (i.e., the second statistics features) generated by performing the discrete Fourier transform and the statistical and integration process on the in-phase polarized discrete data in one sampling dataset |
| 50-65 | 16 initial training features (i.e., the first frequency domain features) generated by performing the discrete Fourier transform on the in-phase polarized discrete data in one sampling dataset |
| 66-75 | 10 initial training features (i.e., the second statistics features) generated by performing the discrete Fourier transform and the statistical and integration process on the quadrature polarized discrete data in one sampling dataset |
| 76-91 | 16 initial training features (i.e., the first frequency domain features) generated by performing the discrete Fourier transform on the quadrature polarized discrete data in one sampling dataset |
| 92-101 | 10 initial training features (i.e., the fourth statistics features) generated by performing the jerk operation, the discrete Fourier transform, and the statistical and integration process on the in-phase polarized discrete data in one sampling dataset |
| 102-117 | 16 initial training features (i.e., the second frequency domain features) generated by performing the jerk operation and the discrete Fourier transform on the in-phase polarized discrete data in one sampling dataset |
| 118-127 | 10 initial training features (i.e., the fourth statistics features) generated by performing the jerk operation, the discrete Fourier transform, and the statistical and integration process on the quadrature polarized discrete data in one sampling dataset |
| 128-143 | 16 initial training features (i.e., the second frequency domain features) generated by performing the jerk operation and the discrete Fourier transform on the quadrature polarized discrete data in one sampling dataset |

According to the example of Table 2, the processor 104 can obtain 144 initial training features respectively corresponding to different feature generation rules. For example, the initial training features numbered as feature numbers 0-9 correspond to the feature generation rule of performing only the statistical and integration process, and the initial training features numbered as feature numbers 118-127 correspond to the feature generation rule of sequentially performing the pre-process, the time domain to frequency domain conversion process, and the statistical and integration process.

Next, referring to FIG. 4B, in step S440, the processor 104 establishes the classification prediction model by using the posture of the experiment living body and the initial training features as training data of the supervised learning algorithm. In the present embodiment, the processor 104 may label the sampling datasets based on the posture of the human body, i.e., "lying face-down" or "lying face-up", and trains a classification prediction model according to the labeled sampling datasets and the corresponding initial training features. When the processor 104 trains the classification prediction model by using the kernel function and the supervised learning algorithm, the correlation feature weightings of the initial training features are also generated. For example, Table 3 shows the correlation feature weightings generated by performing machine learning according to the initial training features shown in Table 2.

to the correlation feature weightings. Specifically, in step S451, based on the feature generation rules of the initial training features, the processor 104 performs a statistical process on the correlation feature weightings of the initial training features to generate a plurality of evaluation values respectively corresponding to the feature generation rules. In other words, the processor 104 performs a statistical process on the correlation feature weightings of the initial training features corresponding to the same one feature generation rule. In addition, the statistical process is performed separately on the correlation feature weightings of the initial training features associated with the I-channel data and on the correlation feature weightings of the initial training features associated with the Q-channel data. Taking Table 3

TABLE 3

| Feature No. | Correlation feature weighting | Feature No. | Correlation feature weighting | Feature No. | Correlation feature weighting | Feature No. | Correlation feature weighting |
| --- | --- | --- | --- | --- | --- | --- | --- |
| 0 | −0.3691 | 20 | −0.1491 | 40 | 1.7267 | 92 | −2.1578 |
| 1 | 0.3523 | 21 | 1.5725 | 41 | −0.3691 | 93 | −0.9318 |
| 2 | 1.6470 | 22 | 0.1010 | 42 | −0.3211 | 94 | −0.0831 |
| 3 | −0.5291 | 23 | 0.0444 | 43 | −0.5007 | 95 | 1.3138 |
| 4 | −1.2899 | 24 | −0.5994 | 44 | −0.7057 | 96 | 1.6755 |
| 5 | 0.1796 | 25 | −1.0104 | 45 | −0.0736 | 97 | −0.0404 |
| 6 | −0.0823 | 26 | −1.3958 | 46 | 0.9589 | 98 | −0.0411 |
| 7 | −0.6683 | 27 | −1.3914 | 47 | −0.5322 | 99 | −0.3527 |
| 8 | −0.1286 | 28 | 0.1189 | 48 | 1.7358 | 100 | −2.1432 |
| 9 | 1.4053 | 29 | 3.6011 | 49 | 1.2697 | 101 | 3.7638 |
| 10 | −0.3981 | 30 | 0.3527 | 66 | 0.5060 | 118 | −0.8976 |
| 11 | 0.0965 | 31 | 0.8763 | 67 | −0.3981 | 119 | −0.0273 |
| 12 | −0.4228 | 32 | −1.1031 | 68 | −0.0318 | 120 | −0.0322 |
| 13 | −1.8473 | 33 | −0.0982 | 69 | 0.4699 | 121 | −0.5668 |
| 14 | 0.9113 | 34 | −0.3731 | 70 | 0.1207 | 122 | −0.0669 |
| 15 | −0.1911 | 35 | 0.3117 | 71 | −0.5061 | 123 | −0.1852 |
| 16 | 1.9313 | 36 | −2.5607 | 72 | 1.1151 | 124 | −0.2621 |
| 17 | 1.3878 | 37 | −2.8831 | 73 | −0.5608 | 125 | −0.2373 |
| 18 | −0.5285 | 38 | −0.3438 | 74 | 0.5176 | 126 | −0.9188 |
| 19 | 1.2453 | 39 | −0.1849 | 75 | 1.3302 | 127 | −0.2002 |
| 50 | −1.1196 | 102 | 2.4891 | 76 | −0.6417 | 128 | −0.2350 |
| 51 | −0.3691 | 103 | 0.1316 | 77 | −0.3981 | 129 | 0.3652 |
| 52 | 0.8019 | 104 | 0.0929 | 78 | 0.8457 | 130 | −0.4593 |
| 53 | 0.1345 | 105 | −0.0599 | 79 | 0.0312 | 131 | −0.0401 |
| 54 | −0.2674 | 106 | 0.1169 | 80 | −0.3896 | 132 | −0.1404 |
| 55 | −0.1759 | 107 | 0.1729 | 81 | 1.1944 | 133 | −0.2795 |
| 56 | 1.0658 | 108 | −0.9318 | 82 | −0.4022 | 134 | −0.0608 |
| 57 | 0.7240 | 109 | −0.0081 | 83 | 0.0883 | 135 | 0.8546 |
| 58 | 0.0394 | 110 | −0.1396 | 84 | −0.1653 | 136 | 0.4119 |
| 59 | −0.1140 | 111 | −0.1548 | 85 | 0.5087 | 137 | −0.9827 |
| 60 | 0.1531 | 112 | −0.9440 | 86 | −0.2392 | 138 | −0.7079 |
| 61 | −0.4490 | 113 | −0.9051 | 87 | 0.0375 | 139 | −0.0397 |
| 62 | −0.1622 | 114 | −0c.3436 | 88 | −0.1957 | 140 | 0.1358 |
| 63 | −0.1067 | 115 | 0.5902 | 89 | −0.1678 | 141 | 0.4844 |
| 64 | −0.0180 | 116 | 0.1924 | 90 | −0.0291 | 142 | 0.2034 |
| 65 | 0.0360 | 117 | 0.1967 | 91 | −0.1273 | 143 | −0.0639 |

Referring to Table 3, the 144 initial training features numbered as feature numbers 0-143 respectively have corresponding correlation feature weightings. For example, the correlation feature weighting $W_9$ of the initial training feature numbered as feature number 9 (i.e., one of the first statistics features) is 1.4053, and the correlation feature weighting $W_{29}$ of the initial training feature numbered as feature number 29 (i.e., one of the third statistics features) is 3.6011. The correlation feature weighting $W_{60}$ of the initial training feature numbered as feature number 60 (i.e., one of the first frequency domain features) is 0.1531, and the correlation feature weighting $W_{136}$ of the initial training feature numbered as feature number 136 (i.e., one of the second frequency domain features) is 0.4119.

In step S450, the processor 104 selects a plurality of preferred features from the initial training features according as an example, feature numbers 0-9 correspond to the same feature generation rule, and the processor 104 performs the statistical process on the correlation feature weightings $W_0$-$W_9$ of the initial training features numbered as feature numbers 0-9 to generate an evaluation value. In the present embodiment, the statistical process may include taking an absolute value of the correlation feature weightings and then taking a mean value. In other words, according to Formula (1), the processor 104 may perform the statistical process on the correlation feature weightings of the initial training features corresponding to the same one feature generation rule.

$$\text{Evaluation value} = \text{avg}(\text{abs}(Wi)) \qquad \text{Formula (1)}$$

where avg(•) represents taking a mean value, abs(•) represents taking an absolute value, and Wi represents the correlation feature weighting. Taking Table 3 as an example, the processor 104 substitutes the correlation feature weightings $W_0$-$W_9$ of the initial training features numbered as feature numbers 0-9 into Formula (1) to generate an evaluation value of 0.66515. The processor 104 substitutes the correlation feature weightings $W_{10}$-$W_{19}$ of the initial training features numbered as feature numbers 10-19 into Formula (1) to generate another evaluation value of 0.896.

In step S452, the processor 104 determines whether the evaluation values satisfy a selection condition to select the preferred features from the initial training features. In an embodiment, the processor 104 may determine whether the evaluation values are greater than a threshold value to determine whether the evaluation values satisfy the selection condition. If an evaluation value is greater than the threshold value, the processor 104 determines that this evaluation value satisfies the selection condition and selects the part of the initial training features associated with the evaluation value as the preferred features. The threshold value may be a predetermined value or may be generated based on all of the calculated evaluation values. For example, the processor 104 may add up all of the evaluation values generated according to Formula (1) and multiply by a percentage value (e.g., 20%) to generate the threshold value.

Taking Table 3 as an example, it is assumed that after the processor 104 performs the statistical calculation on the correlation feature weightings $W_0$-$W_{143}$ of all of the initial training features, 12 evaluation values A1 to A12 respectively corresponding to 12 sets of the correlation feature weightings $W_0$-$W_9$, $W_{10}$-$W_{19}$, $W_{20}$-$W_{29}$, $W_{30}$-$W_{39}$, $W_{40}$-$W_{49}$, $W_{66}$-$W_{75}$, $W_{92}$-$W_{101}$, $W_{118}$-$W_{127}$, $W_{50}$-$W_{65}$, $W_{102}$-$W_{117}$, $W_{76}$-$W_{91}$, and $W_{128}$-$W_{143}$ may be generated. The processor 104 may first add up the evaluation values A1 to A12 and multiply by 20% to generate the threshold value TH. Then, the processor 104 may sequentially determine whether the evaluation values A1 to A12 are greater than the threshold value TH to determine whether to select the initial training features associated with the evaluation values A1 to A12 as the preferred features. For example, if the evaluation value A7 generated based on the correlation feature weightings $W_{92}$-$W_{101}$ of the initial training features of feature numbers 92-101 is greater than the threshold value TH, the initial training features of feature numbers 92-101 are selected as the preferred features.

It is noted that, in an embodiment, the initial training features associated with the evaluation values satisfying the selection condition may include the initial training features generated based on the I-channel data and the Q-channel data, and the processor 104 may select the preferred features associated with the in-phase polarized discrete data or the quadrature polarized discrete data therefrom. In other words, the processor 104 may select the initial training features corresponding to one of the I-channel data and the Q-channel data as the preferred features to thereby reduce the data processing amount of subsequently detecting the posture of the living body using the classification prediction model.

After the preferred features are selected, in step S460, the processor 104 establishes another classification prediction model according to the posture of the experiment living body and the preferred features. The operation of step S460 is similar to step S440, and the difference lies in the number of features for training the model. Specifically, in step S460, the another classification prediction model is trained according to the filtered preferred features. Here, the processor 104 may test the another classification prediction model to determine whether the classification accuracy of the another classification prediction model is sufficient, so as to determine whether to perform feature filtering and model training again. Alternatively, the processor 104 may test the another classification prediction model to determine whether the classification accuracy of the another classification prediction model is sufficient, so as to determine whether to select other additional preferred features from the initial training features.

At the application stage of actual detection, in step S470, the processor 104 determines a posture of a detection living body based on the another classification prediction model. The detection living body is similarly a human body lying on a bed. Specifically, in step S471, the antenna 101 receives another RF signal reflected by the detection living body, and the RF signal processing circuit 102 obtains a plurality of other raw sampling data of the another RF signal. In step S472, the processor 104 generates a plurality of detection features according to the other raw sampling data based on the feature generation rules of the preferred features. Compared to step S330, the processor 104 may generate a smaller number of features according to the lower data processing amount and input the filtered number of features to the classifier to determine whether the posture of the human body is lying face-up or lying face-down. In step S473, the processor 104 inputs the detection features to the another classification prediction model to determine the posture of the detection living body.

In summary of the above, in the embodiments of the disclosure, the posture of the detection living body with vital signs may be detected through radar sensing techniques and machine learning. In addition, in the embodiments of the disclosure, as the classification accuracy of the classification prediction model is maintained at a certain level, a part of the available features may be flexibly selected to reduce the data computation amount, which contributes to reduction of the computation amount required for machine learning and realization of rapid detection. Further, the machine learning algorithm adopted in the living body detection method of the disclosure is not limited to the aforementioned support vector machine algorithm. For example, in another embodiment of the disclosure, a special time recurrent neural network (RNN) using long short term memory (LSTM) is adopted to enhance the identification accuracy of dynamic recognition.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A living body detection method comprising:
   receiving an RF signal reflected by an experiment living body and generating a plurality of raw sampling data of the RF signal;
   performing a feature extraction process according to the raw sampling data to generate a plurality of initial training features of a plurality of sampling datasets, wherein the initial training features respectively correspond to a plurality of feature generation rules;
   establishing a classification prediction model according to a posture of the experiment living body and the initial training features, and obtaining a plurality of correlation feature weightings respectively corresponding to the initial training features;

selecting a plurality of preferred features corresponding to at least one of the feature generation rules from the initial training features according to the correlation feature weightings;
establishing another classification prediction model according to the posture of the experiment living body and the preferred features; and
determining a posture of a detection living body based on the another classification prediction model,
wherein the step of receiving the RF signal reflected by the experiment living body and obtaining the raw sampling data of the RF signal comprises:
generating an in-phase polarized signal and a quadrature polarized signal according to the RF signal; and
respectively sampling the in-phase polarized signal and the quadrature polarized signal to generate a plurality of in-phase polarized discrete data and a plurality of quadrature polarized discrete data, wherein the raw sampling data comprise the in-phase polarized discrete data and the quadrature polarized discrete data.

2. The living body detection method according to claim 1, wherein after the step of receiving the RF signal reflected by the experiment living body and obtaining the raw sampling data of the RF signal, the method further comprises:
extracting the raw sampling data according to a window length, a sample size, and a sample overlap time to generate the sampling datasets, wherein the sampling datasets respectively comprise the raw sampling data that match the sample size in the window length.

3. The living body detection method according to claim 2, wherein the sampling datasets comprise a first sampling dataset and a second sampling dataset, the raw sampling data in the first sampling dataset partially overlap with the raw sampling data in the second sampling dataset, an extraction time of the first sampling dataset differs from an extraction time of the second sampling dataset by a predetermined time interval, and the predetermined time interval is determined according to the sample size and the sample overlap time.

4. The living body detection method according to claim 1, wherein the step of performing the feature extraction process according to the raw sampling data to generate the initial training features of the sampling datasets comprises:
performing a statistical and integration process respectively on the raw sampling data in the sampling datasets to generate a plurality of first statistics features of the sampling datasets;
performing a time domain to frequency domain conversion process respectively on the raw sampling data in the sampling datasets to generate a plurality of first discrete frequency domain data, so as to obtain a plurality of first frequency domain features of the sampling datasets from the first discrete frequency domain data; and
performing a statistical and integration process respectively on the first discrete frequency domain data to generate a plurality of second statistics features of the sampling datasets.

5. The living body detection method according to claim 4, wherein the step of performing the feature extraction process according to the raw sampling data to generate the initial training features of the sampling datasets comprises:
performing a pre-process respectively on the raw sampling data in the sampling datasets to generate a plurality of pre-processed data;
performing a statistical and integration process respectively on the pre-processed data of the sampling datasets to generate a plurality of third statistics features of the sampling datasets;
performing a time domain to frequency domain conversion process respectively on the pre-processed data of the sampling datasets to generate a plurality of second discrete frequency domain data, so as to obtain a plurality of second frequency domain features of the sampling datasets from the second discrete frequency domain data; and
performing a statistical and integration process respectively on the second discrete frequency domain data to generate a plurality of fourth statistics features of the sampling datasets.

6. The living body detection method according to claim 1, wherein the step of establishing the classification prediction model according to the posture of the experiment living body and the initial training features, and obtaining the correlation feature weightings respectively corresponding to the initial training features comprises:
establishing the classification prediction model by using the posture of the experiment living body and the initial training features as training data of a supervised learning algorithm, wherein the correlation feature weightings respectively corresponding to the initial training features are generated based on a kernel function operated with the supervised learning algorithm.

7. The living body detection method according to claim 1, wherein the step of selecting the preferred features from the initial training features according to the correlation feature weightings comprises:
performing a statistical process on the correlation feature weightings of the initial training features based on the feature generation rules of the initial training features to generate a plurality of evaluation values; and
determining whether the evaluation values satisfy a selection condition to select the preferred features from the initial training features.

8. The living body detection method according to claim 7, wherein the selection condition comprises whether the evaluation values are greater than a threshold value, and the threshold value is generated by adding up the evaluation values and multiplying by a percentage value.

9. The living body detection method according to claim 1, wherein the step of determining the posture of the detection living body based on the another classification prediction model comprises:
receiving another RF signal reflected by the detection living body, and obtaining a plurality of other raw sampling data of the another RF signal;
generating a plurality of detection features according to the other raw sampling data based on at least one of the feature generation rules of the preferred features; and
inputting the detection features to the another classification prediction model to determine the posture of the detection living body.

10. A living body detection system comprising:
an antenna, receiving an RF signal reflected by an experiment living body;
an RF signal processing circuit, coupled to the antenna and generating a plurality of raw sampling data of the RF signal;
a storage circuit, storing a plurality of modules; and
a processor, coupled to the storage circuit and the RF signal processing circuit and accessing the modules to perform steps below:

performing a feature extraction process according to the raw sampling data to generate a plurality of initial training features of a plurality of sampling datasets, wherein the initial training features respectively correspond to a plurality of feature generation rules;

establishing a classification prediction model according to a posture of the experiment living body and the initial training features, and obtaining a plurality of correlation feature weightings respectively corresponding to the initial training features;

selecting a plurality of preferred features corresponding to at least one of the feature generation rules from the initial training features according to the correlation feature weightings;

establishing another classification prediction model according to the posture of the experiment living body and the preferred features; and determining a posture of a detection living body based on the another classification prediction model, wherein the RF signal processing circuit generates an in-phase polarized signal and a quadrature polarized signal according to the RF signal and respectively samples the in-phase polarized signal and the quadrature polarized signal to generate a plurality of in-phase polarized discrete data and a plurality of quadrature polarized discrete data, wherein the raw sampling data comprise the in-phase polarized discrete data and the quadrature polarized discrete data.

11. The living body detection system according to claim 10, wherein the processor is further configured to:
extract the raw sampling data according to a window length, a sample size, and a sample overlap time to generate the sampling datasets, wherein the sampling datasets respectively comprise the raw sampling data that match the sample size in the window length.

12. The living body detection system according to claim 11, wherein the sampling datasets comprise a first sampling dataset and a second sampling dataset, the raw sampling data in the first sampling dataset partially overlap with the raw sampling data in the second sampling dataset, an extraction time of the first sampling dataset differs from an extraction time of the second sampling dataset by a predetermined time interval, and the predetermined time interval is determined according to the sample size and the sample overlap time.

13. The living body detection system according to claim 10, wherein the processor is further configured to:
perform a statistical and integration process respectively on the raw sampling data in the sampling datasets to generate a plurality of first statistics features of the sampling datasets;
perform a time domain to frequency domain conversion process respectively on the raw sampling data in the sampling datasets to generate a plurality of first discrete frequency domain data, so as to obtain a plurality of first frequency domain features of the sampling datasets from the first discrete frequency domain data; and
perform a statistical and integration process respectively on the first discrete frequency domain data to generate a plurality of second statistics features of the sampling datasets.

14. The living body detection system according to claim 13, wherein the processor is further configured to:
perform a pre-process respectively on the raw sampling data in the sampling datasets to generate a plurality of pre-processed data;
perform a statistical and integration process respectively on the pre-processed data of the sampling datasets to generate a plurality of third statistics features of the sampling datasets;
perform a time domain to frequency domain conversion process respectively on the pre-processed data of the sampling datasets to generate a plurality of second discrete frequency domain data, so as to obtain a plurality of second frequency domain features of the sampling datasets from the second discrete frequency domain data; and
perform a statistical and integration process respectively on the second discrete frequency domain data to generate a plurality of fourth statistics features of the sampling datasets.

15. The living body detection system according to claim 10, wherein the processor is further configured to:
establish the classification prediction model by using the posture of the experiment living body and the initial training features as training data of a supervised learning algorithm, wherein the correlation feature weightings respectively corresponding to the initial training features are generated based on a kernel function operated with the supervised learning algorithm.

16. The living body detection system according to claim 10, wherein the processor is further configured to:
perform a statistical process on the correlation feature weightings of the initial training features based on the feature generation rules of the initial training features to generate a plurality of evaluation values; and
determine whether the evaluation values satisfy a selection condition to select the preferred features from the initial training features.

17. The living body detection system according to claim 16, wherein the selection condition comprises whether the evaluation values are greater than a threshold value, and the threshold value is generated by adding up the evaluation values and multiplying by a percentage value.

18. The living body detection system according to claim 10, wherein the processor is further configured to:
receive another RF signal reflected by the detection living body, and obtain a plurality of other raw sampling data of the another RF signal;
generate a plurality of detection features according to the other raw sampling data based on at least one of the feature generation rules of the preferred features; and
input the detection features to the another classification prediction model to determine the posture of the detection living body.

19. A living body detection method comprising:
receiving an RF signal reflected by an experiment living body and generating a plurality of raw sampling data of the RF signal;
performing a feature extraction process according to the raw sampling data to generate a plurality of initial training features of a plurality of sampling datasets, wherein the initial training features respectively correspond to a plurality of feature generation rules;
establishing a classification prediction model according to a posture of the experiment living body and the initial training features, and obtaining a plurality of correlation feature weightings respectively corresponding to the initial training features;
selecting a plurality of preferred features corresponding to at least one of the feature generation rules from the initial training features according to the correlation feature weightings;

establishing another classification prediction model according to the posture of the experiment living body and the preferred features; and determining a posture of a detection living body based on the another classification prediction model, wherein after the step of receiving the RF signal reflected by the experiment living body and obtaining the raw sampling data of the RF signal, the method further comprises:

extracting the raw sampling data according to a window length, a sample size, and a sample overlap time to generate the sampling datasets, wherein the sampling datasets respectively comprise the raw sampling data that match the sample size in the window length.

20. The living body detection method according to claim 19, wherein the sampling datasets comprise a first sampling dataset and a second sampling dataset, the raw sampling data in the first sampling dataset partially overlap with the raw sampling data in the second sampling dataset, an extraction time of the first sampling dataset differs from an extraction time of the second sampling dataset by a predetermined time interval, and the predetermined time interval is determined according to the sample size and the sample overlap time.

21. A living body detection system comprising:

an antenna, receiving an RF signal reflected by an experiment living body;

an RF signal processing circuit, coupled to the antenna and generating a plurality of raw sampling data of the RF signal;

a storage circuit, storing a plurality of modules; and a processor, coupled to the storage circuit and the RF signal processing circuit and accessing the modules to perform steps below:

performing a feature extraction process according to the raw sampling data to generate a plurality of initial training features of a plurality of sampling datasets, wherein the initial training features respectively correspond to a plurality of feature generation rules;

establishing a classification prediction model according to a posture of the experiment living body and the initial training features, and obtaining a plurality of correlation feature weightings respectively corresponding to the initial training features;

selecting a plurality of preferred features corresponding to at least one of the feature generation rules from the initial training features according to the correlation feature weightings;

establishing another classification prediction model according to the posture of the experiment living body and the preferred features; and determining a posture of a detection living body based on the another classification prediction model, wherein the processor is further configured to:

extract the raw sampling data according to a window length, a sample size, and a sample overlap time to generate the sampling datasets, wherein the sampling datasets respectively comprise the raw sampling data that match the sample size in the window length.

22. The living body detection system according to claim 11, wherein the sampling datasets comprise a first sampling dataset and a second sampling dataset, the raw sampling data in the first sampling dataset partially overlap with the raw sampling data in the second sampling dataset, an extraction time of the first sampling dataset differs from an extraction time of the second sampling dataset by a predetermined time interval, and the predetermined time interval is determined according to the sample size and the sample overlap time.

* * * * *